United States Patent
Raupach

(10) Patent No.: US 7,315,604 B2
(45) Date of Patent: Jan. 1, 2008

(54) METHOD FOR AN X-RAY DEVICE AND COMPUTER TOMOGRAPH FOR REDUCING BEAM HARDENING ARTIFACTS FROM A GENERATED IMAGE OF AN OBJECT

(75) Inventor: Rainer Raupach, Adelsdorf (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/360,772

(22) Filed: Feb. 24, 2006

(65) Prior Publication Data

US 2006/0203956 A1    Sep. 14, 2006

(30) Foreign Application Priority Data

Feb. 25, 2005    (DE) .................. 10 2005 008 767

(51) Int. Cl.
*H05G 1/00* (2006.01)
*H05G 1/64* (2006.01)

(52) U.S. Cl. .................. 378/5; 378/19; 378/98.9
(58) Field of Classification Search .............. 378/4, 378/5, 19, 98.7, 98.9, 901
See application file for complete search history.

(56) References Cited

U.S. PATENT DOCUMENTS

| 2003/0053597 | A1 | 3/2003 | Flohr et al. | |
|---|---|---|---|---|
| 2004/0066881 | A1* | 4/2004 | Reddy et al. | 378/5 |
| 2004/0092814 | A1* | 5/2004 | Hsieh et al. | 600/425 |
| 2004/0101088 | A1* | 5/2004 | Sabol et al. | 378/4 |
| 2004/0102688 | A1 | 5/2004 | Walker et al. | |
| 2004/0136491 | A1* | 7/2004 | Iatrou et al. | 378/4 |
| 2004/0228451 | A1* | 11/2004 | Wu et al. | 378/207 |
| 2006/0109949 | A1* | 5/2006 | Tkaczyk et al. | 378/4 |

FOREIGN PATENT DOCUMENTS

DE    100 48 775 A1    9/2000

* cited by examiner

*Primary Examiner*—Edward J. Glick
*Assistant Examiner*—Irakli Kiknadze
(74) *Attorney, Agent, or Firm*—Harness, Dickey & Pierce

(57) ABSTRACT

A method is disclosed for an x-ray device and a computer tomograph for suppressing beam hardening artifacts in a generated image of an object, for example in a tomogram of a patient. In the method, N measured values are acquired relating to N different energy ranges of the x-radiation. Further, one pseudomonochromatic measured value is calculated in each case from the N measured values such that there is generated from different projection directions on the basis of the calculated pseudomonochromatic measured values, an image in which beam hardening artifacts are substantially suppressed.

20 Claims, 4 Drawing Sheets

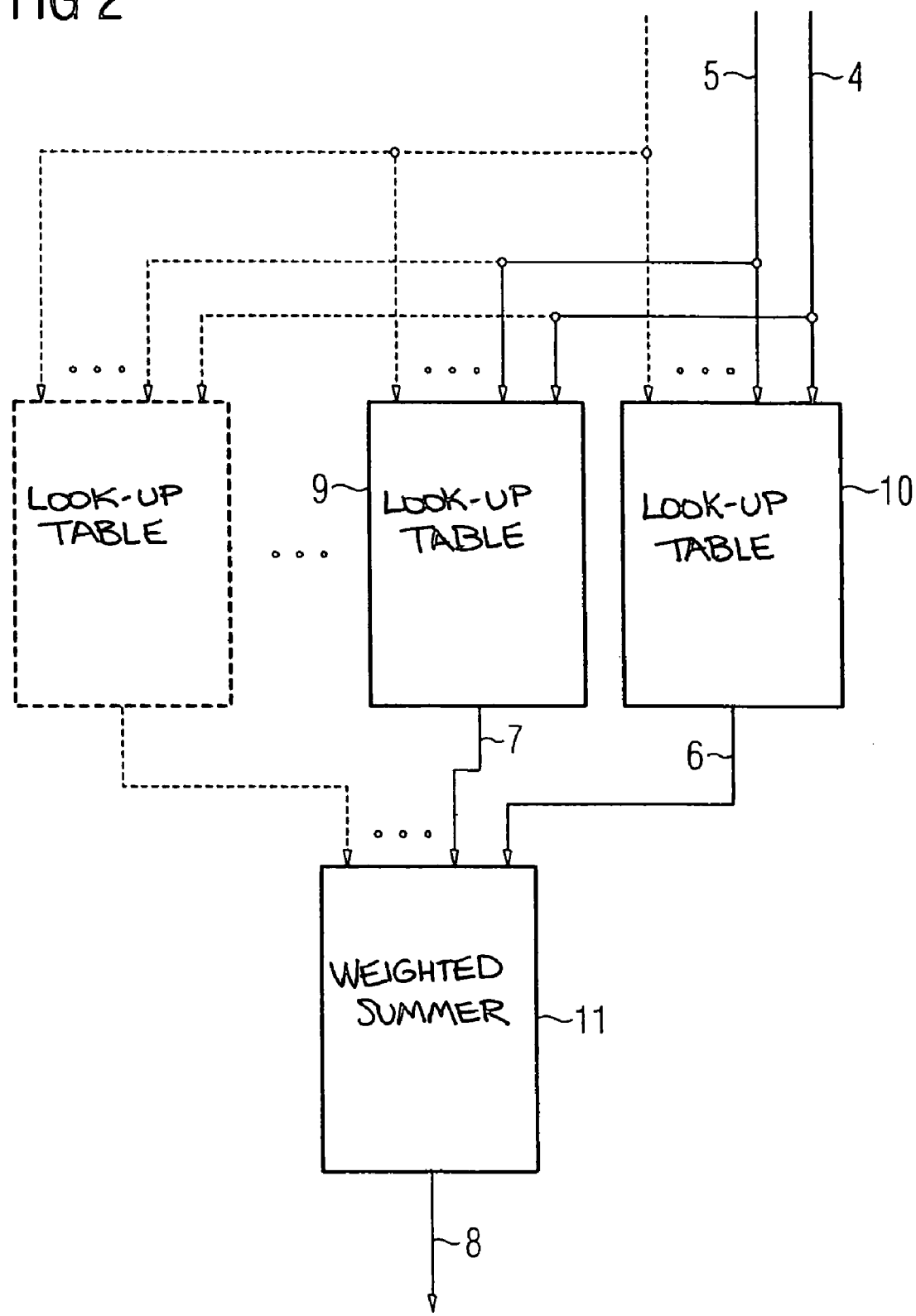

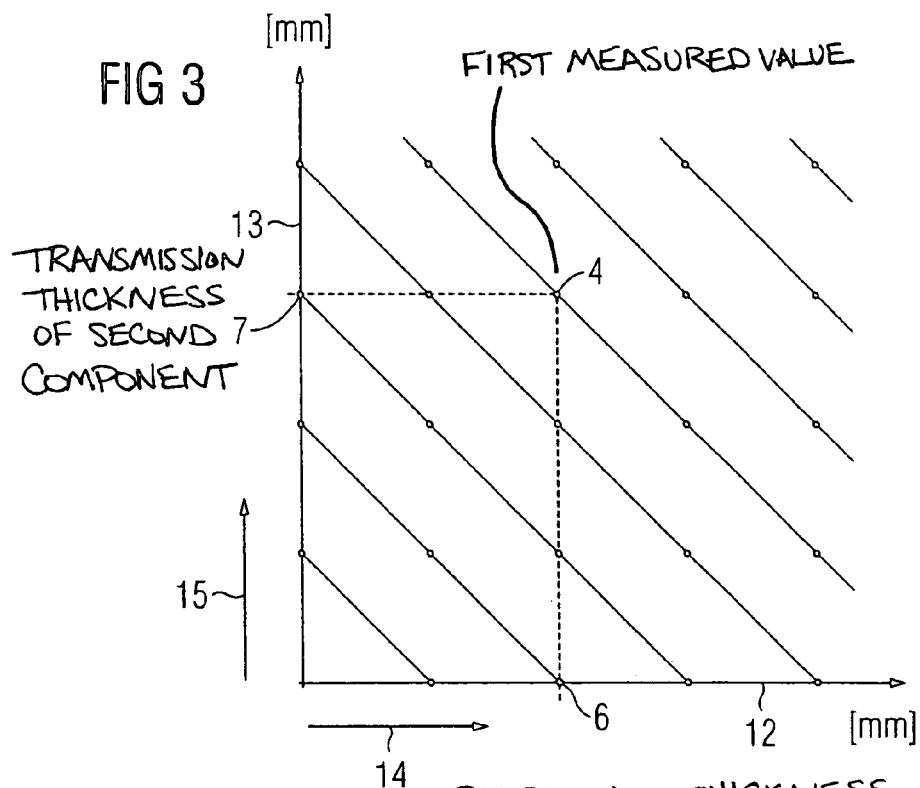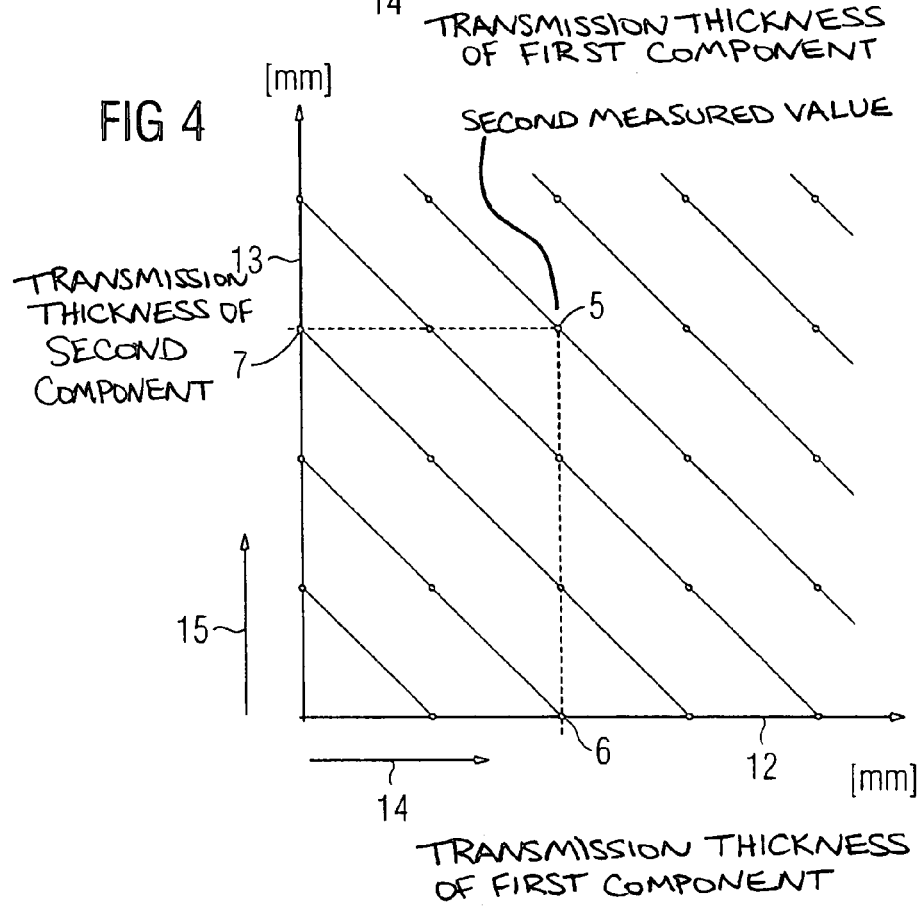

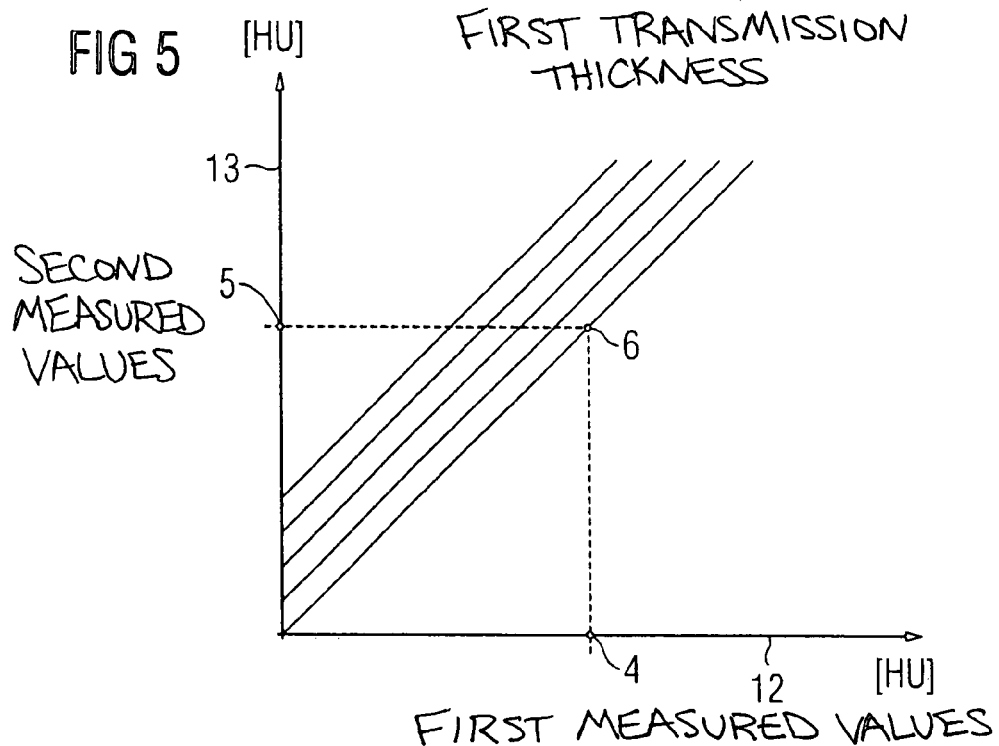
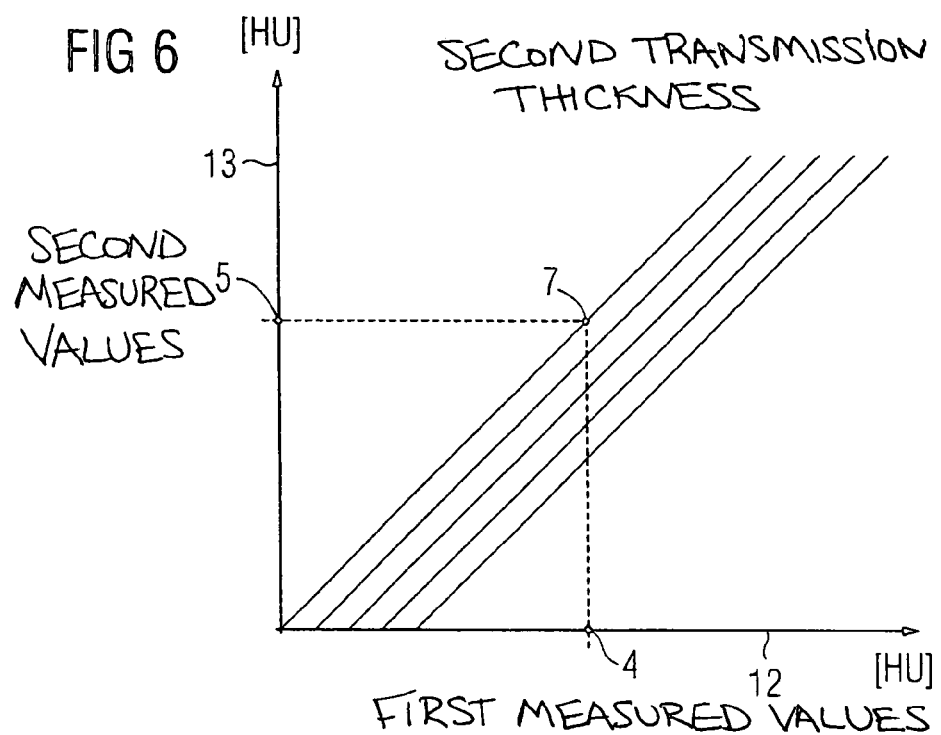

METHOD FOR AN X-RAY DEVICE AND COMPUTER TOMOGRAPH FOR REDUCING BEAM HARDENING ARTIFACTS FROM A GENERATED IMAGE OF AN OBJECT

The present application hereby claims priority under 35 U.S.C. §119 on German patent application number DE 10 2005 008 767.1 filed Feb. 25, 2005, the entire contents of which is hereby incorporated herein by reference.

FIELD

The invention generally relates to a method for an x-ray device for reducing beam hardening artifacts in a generated image of an object. In such a case, for example, x-radiation may be generated by an x-ray emitter, and measured values may be acquired as a function of an attenuation of the x-radiation passing through the object from different projection directions by a detector formed from a number of detector elements. The invention also generally relates to a computer tomograph having means for carrying out such a method.

BACKGROUND

The x-radiation generated by the x-ray emitter of an x-ray device and which trans-irradiates the object is not monochromatic, but has an energy spectrum dependent on the tube voltage set. When x-radiation is absorbed during passage through matter, less energetic x-rays are absorbed more strongly than more energetic x-rays because of an energy dependence of the absorption coefficients. This effect, denoted as beam hardening, is substantially dependent on the mean atomic number of the trans-irradiated matter and on the spectral distribution of the x-radiation. This effect is qualitatively higher with increasing atomic number of the matter and with dropping x-ray proton energy.

The object trans-irradiated by the x-radiation is constructed as a rule from various components that partially have quite different absorption coefficients. Moreover, the components are also not distributed in a rotationally symmetrical fashion about a center of rotation of the x-ray device, and so the components are trans-irradiated in different sequence when the projection angles of the recording system are differently set. Because of the beam hardening, no ideal exponential relationship results between the trans-irradiated thickness and signal attenuation in accordance with the attenuation law for monochromatic radiation.

The detector does not acquire the spectral distribution of the x-radiation passing through the object, but only the total energy or the total quantum number of the x-ray photons, and so systematic measured value inconsistencies result that are reflected in typical beam hardening artifacts in the images generated from the measured values. Such inconsistencies can be visualized by artifacts along rays that experience a large hardening effect.

Image artifacts occur, for example, during an examination of a patient's head. In the corresponding tomograms, dark strips are visible in the soft-part tissue between thick bone layers, in particular in the region of the basicranial bone, and these greatly complicate a diagnosis.

Image-correcting measures are necessary for this reason so that the beam hardening artifacts are largely eliminated.

Established methods for computer tomographs for the purpose of eliminating beam hardening artifacts from tomograms of an object having a number of components operate iteratively and require a substantial computational outlay. In a first method step, a temporary tomogram is reconstructed from the measured values of an object that have been obtained from various projection directions. Subsequently, the various components, for example, the bone portions and tissue portions, in the temporary tomogram are identified by way of a segmentation in the pixel image of the layer such that a correction of the measured values can be carried out after reprojection of the component images. Subsequently, there is reconstructed, in turn, from the measured values thus corrected a tomogram in which radiation artifacts continue to be present only in an attenuated form. In order for the beam hardening artifacts to be removed sufficiently well from the tomogram, it is necessary in the case of specific methods to repeat the sequence of segmentation, reprojection, correction and reconstruction of the tomogram until there is a convergence.

By comparison with a simple reconstruction of a tomogram, there is a tripling of the numerical outlay even in the case of only a single iteration step for the known method for correcting beam hardening artifacts, and so it is not always possible to carry out such corrections. The applicability of iterative algorithms for removing beam hardening artifacts becomes all the more difficult, moreover, the more complicated the beam path of the x-radiation through the object. There is also a need for 3D forward projectors or appropriate ray tracers in the field of 3D backprojections, and these are likewise associated with a high numerical outlay.

DE 103 56 116 states a further method for a computer tomograph for reducing beam hardening artifacts. The method includes the acquisition of measured data of an object from various projection directions for two different spectra of the x-radiation, a reconstruction of at least a first and a second temporary energy image, a transformation of the second temporary energy image into a first transformed energy image, and a combination of the first temporary energy image with the first transformed energy image in order to generate a combined first energy image in which beam hardening artifacts are reduced. This method can also be carried out only with a very high numerical outlay.

SUMMARY

It is an object of at least one embodiment of the present invention to specify a method for an x-ray device and/or a computer tomograph with the aid of which an efficient reduction of beam hardening artifacts from a generated image of an object is possible.

An object of at least one embodiment may be achieved by way of a method for an x-ray device and/or by way of a computer tomograph for reducing beam hardening artifacts from a generated image of an object.

At least one embodiment of the invention proceeds from the finding that a correction of measured values of an x-ray device for reducing beam hardening artifacts is possible even without using an iterative process and without calculating temporary energy images when at least two measured values relating to at least two different energy ranges of the x-radiation are acquired per projection direction relative to each detector element of a detector of the x-ray device. In this case, a correction of each measured value can be determined, for example, by reading out a corrected value from at least one lookup table, the corrected value corresponding to a pseudomonochromatic measured value that takes account of the beam hardening for at least two components upon passage of the x-radiation through the object.

The method according to at least one embodiment of the invention, in which x-radiation is generated and in which the measured values are acquired from the detector, formed from detector elements, as a function of an attenuation of the x-radiation passing through the object from different projection directions, consequently comprises method steps in which:

a) N measured values relating to N different energy ranges of the x-radiation are acquired per projection direction relative to each of the detector elements, where $N>=2$, b) one pseudomonochromatic measured value is respectively determined relative to each of the detector elements from the acquired N measured values, and c) there is reconstructed from the pseudomonochromatic measured values thus determined for the detector elements an image in which the beam hardening artifacts are substantially suppressed.

The correction of the beam hardening artifacts is therefore performed without a complicated numerical iteration process and without calculating temporary energy images directly on the basis of measured values acquired by the detector elements, without the need for a reconstruction of a temporary image for example a tomogram. The correction can therefore be carried out in step with scanning the object.

The N measured values relating to the N different energy ranges of the x-radiation can be acquired in a simple way by way of N differently set spectra of the x-radiation. In a further advantageous variant of at least one embodiment of the invention, it is likewise conceivable for the measured values to be acquired for an unchanged spectrum of the x-radiation, but in various energy windows of an energy-resolving detector.

The determination of the pseudomonochromatic measured value from the N measured values advantageously includes a determination of N transmission thicknesses of N different components, the N different components having differing absorption properties on the basis of different mean atomic numbers for thicknesses.

The transmission thicknesses of the N different components of the object can be determined in a simple way relative to each measured value independently of the sequence in which the components are trans-irradiated by the x-radiation. The determination of the transmission thicknesses offers the advantage, in particular, that these derived measured variables are not influenced by the effect of beam hardening.

The pseudomonochromatic measured value is preferably calculated from a sum of the N transmission thicknesses, weighted in each case with a weighting coefficient, of the N different components. The weighting coefficient is here advantageously an absorption coefficient of the x-radiation that is assigned to the component.

In an advantageous variant of at least one embodiment of the invention, the N transmission thicknesses of the N different components are determined from N lookup tables with in each case N input values and one output value, the N input values being the N measured values corresponding to the N spectral components of the x-radiation, and the output value being the transmission thickness of the respective component. Reading out a value from an N-dimensional lookup table requires only a very short computing time, and so the determination of the N transmission thicknesses of the N components can keep in step with scanning.

Instead of the lookup tables, it is possible alternatively to make use in each case of a suitable polynomial for determining the transmission thickness of the N components from the N measured values.

The N lookup tables are preferably determined in a simple way by virtue of the fact that the N measured values relating to different energy ranges of the x-radiation are simulated and stored in the form of an N-dimensional matrix, the transmission thicknesses of the N different components being varied during the simulation, and the N-dimensional matrices thus determined subsequently being transformed into modified matrices that belong to inverted imagings of the images, defined by the N-dimensional matrices, of N measured values onto N transmission thicknesses. In this case, one of the N lookup tables is formed from each of the N modified matrices.

As an alternative to the N lookup tables, which are used to determine the N transmission thicknesses of the N components of the object, in order to determine therefrom the pseudomonochromatic measured value independent of the beam hardening, it is likewise advantageously provided to determine the pseudomonochromatic measured value directly from a single lookup table with in each case N input values and one output value, the N input values being the N measured values of the N different spectra of the x-radiation, and the output value being the pseudomonochromatic measured value.

In an advantageous refinement of at least one embodiment of the invention, the output value can be interpolated from entries of the respective lookup table. In this case, it is not necessary to take account of all the possible quasi-continuous measured values as input values when generating the lookup table. Rather, it is possible to interpolate the output value matching the measured values, or the matching pseudomonochromatic measured value from the auxiliary output values of those input values that are determined from the next largest and from the next smallest input value, by comparison with the measured value, of the lookup table.

The interpolation of the output value assigned to the measured value can be determined in a particularly expedient way by means of a multilinear interpolation of the dimension N of the auxiliary output values.

The respective lookup table can advantageously be represented by a polynomial that describes a mathematical relationship between the input values and the output value of the lookup table. The use of a polynomial instead of a lookup table for determining transmission thicknesses is possible in conjunction with a low storage requirement when taking account of a high number of different components of an object.

The x-radiation is preferably generated by an x-ray emitter in the form of an x-ray tube. The different spectra of x-radiation can be generated in this case by differently set tube voltages in an advantageous refinement of at least one embodiment of the invention.

In the case when N is equal to two, and the object to be examined essentially has only two components, specifically bone and water, a first spectrum of the x-radiation is advantageously generated for the purpose of acquiring in each case a first measured value with the tube voltage set to 80 kV, and a second spectrum of the x-radiation is generated for the purpose of acquiring a second measured value with the tube voltage set to 140 kV.

It is assumed below without restriction of generality that the x-ray device is a computer tomograph. However, this method can also be used in principle for other types of x-ray devices, in which a plurality of measured values of x-radiation passing through an object are acquired from different projection directions in order to generate an image on the basis of the measured values thus acquired.

BRIEF DESCRIPTION OF THE DRAWINGS

Example embodiments and further advantageous refinements of the invention are discussed below and are illustrated in the following schematic drawings:

FIG. 2 shows in outline form a determination of a pseudomonochromatic measured value for the purpose of correcting beam hardening artifacts, for example for two acquired measured values of a detector element;

FIG. 3 shows equipotential lines of simulated measured values of a first spectrum of the x-radiation, as a function of the transmission thicknesses of two components;

FIG. 4 shows equipotential lines of simulated measured values of a second spectrum of x-radiation, as a function of the transmission thicknesses of two components, in the form of a diagram;

FIG. 5 shows transmission thickness of the first component as a function of the measured values relating to the first and to the second spectral component of the x-radiation; and FIG. 6 shows transmission thickness of the second component as a function of the measured values relating to the first and to the second spectral component of the x-radiation.

DETAILED DESCRIPTION OF THE EXAMPLE EMBODIMENTS

Figure 1:
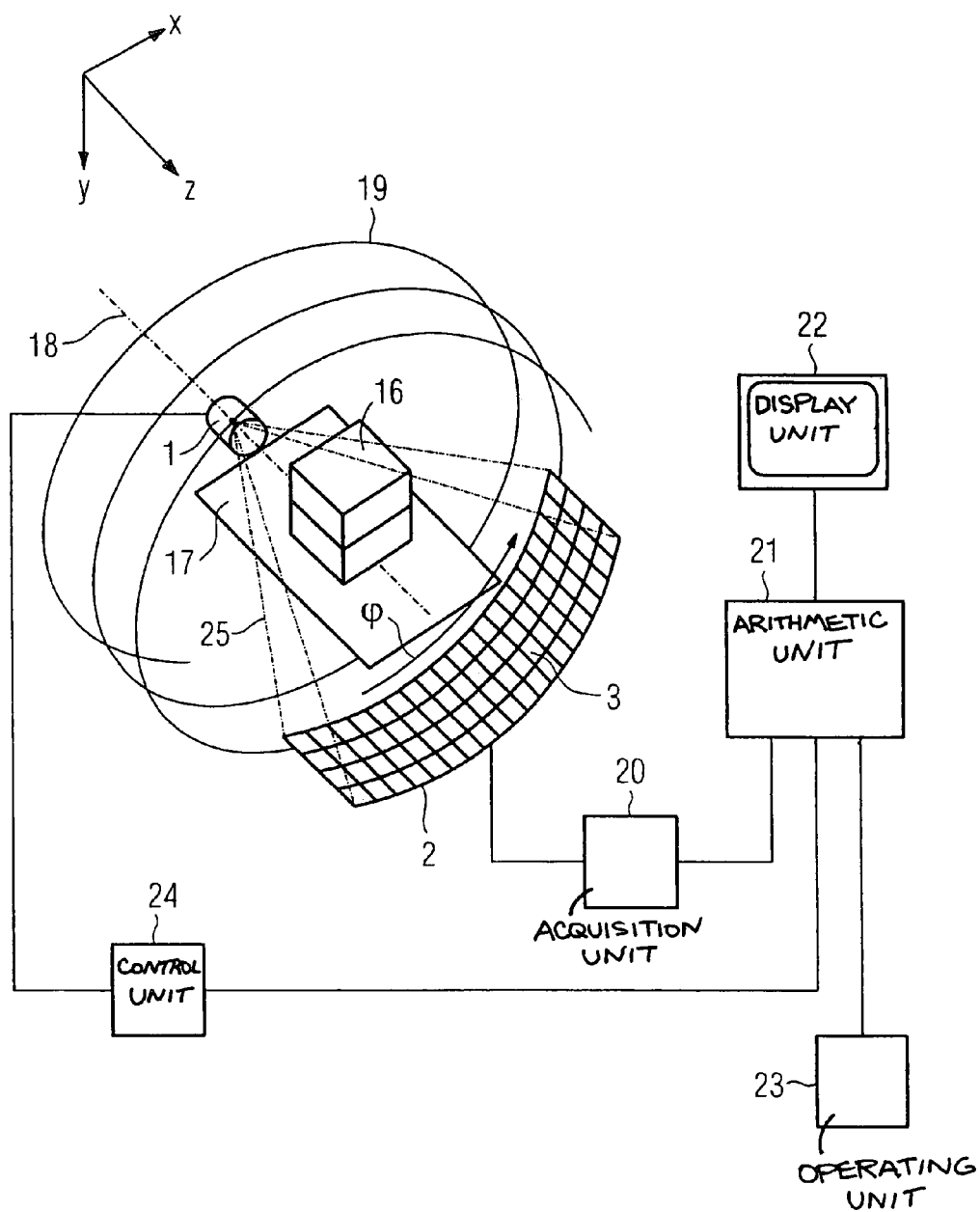
FIG. 1 shows an x-ray device in an illustration that is partially a block diagram and partially in perspective and that is suitable for carrying out at least one embodiment of the inventive method.

FIG. 1 shows an x-ray device, here a computer tomograph, in a view that is partially a block diagram and partially in perspective. A bearing device of the computer tomograph comprises a moveable table plate 17 by which an object 16 to be examined, for example a patient, can be moved through an opening in the housing of the computer tomograph into a measurement area 25 of a recording system 1, 2 assigned to the computer tomograph. The object 16 and the measurement area 25 of the recording system 1, 2 can be displaced relative to one another in this way.

The recording system 1, 2 has an x-ray emitter 1 for example an x-ray tube, and a detector 2 that is arranged opposite the latter and includes a number of detector elements 3 lined up to form columns and rows. The x-ray emitter 1 generates a fan-shaped x-ray beam. The x-ray beam penetrates the object 16 positioned in the measurement area 25 of the recording system 1, 2, and impinges on the detector elements 3 of the detector 2.

The detector elements 3 each generate an attenuation value that is dependent on the attenuation of the x-radiation passing through the measurement area 25 and is denoted below as measured value. The conversion of the x-radiation into measured values is performed, for example, by way of a photodiode optically coupled to a scintillator, or by way of a directly converting semiconductor. A set of measured values of the detector 2 that are recorded for a specific position of the x-ray emitter 1 relative to the object 16 is denoted as "projection".

Located in the interior of the computer tomograph is a gantry (not illustrated) on which the recording system 1, 2 is arranged. The gantry can be rotated about the system axis 18 of the computer tomograph by way of a drive unit (not illustrated) at a high rate of rotation. A multiplicity of projections of the object 16 can be prepared in this way from different projection directions. In particular, an examination area of the object 16 that is greater than the measurement area 25 formed by the recording system 1, 2 can be scanned by rotating the gantry while simultaneously continuously feeding the object 16 in the direction of the system axis 18. The measured values of the object 16 obtained during the spiral scanning 19 from different projection directions can be transformed into tomograms or volume images by computation and be displayed visually by an operator on a display unit 22.

However, the computer tomograph can also be operated in another way deviating from the spiral scanning 19. For example, it is possible to conceive that the object 16 is scanned without displacing the table plate 17 merely by rotating the recording system 1, 2. This type of scanning is used, for example, in the case of cardiological examinations in which cyclic movement cycles of the heart are examined. The operating parameters required for scanning can be prescribed by an operator with the aid of an operating unit 23, the operating unit 23 being connected to an arithmetic unit 21.

The object 16 to be examined generally has various components of matter that partly have entirely different absorption coefficients. The x-radiation generated by the x-ray emitter 1 and which trans-irradiates the object 16 is not monochromatic, but has a spectrum dependent on a tube voltage. Low-energy x-radiation is more strongly attenuated upon passage through matter or upon passage through the object than is high-energy x-radiation. Beam hardening artifacts in the resultant image that is generated are produced by virtue of the fact that different attenuations of the x-radiation are yielded for the same object 16, depending on the sequence in which the matter was trans-irradiated. The measured value inconsistencies resulting therefrom lead to beam hardening artifacts.

The beam hardening artifacts can be corrected when a plurality of measured values relating to different energy ranges of the x-radiation are acquired relative to each detector element 3 in relation to each projection direction. In principal, N components of the trans-irradiated object 16 can be compensated with reference to the beam hardening effect from N measured values acquired relative to different energy ranges.

The acquisition of measured values relating to different energy ranges of the x-radiation is possible in various ways. Thus, for example, it is conceivable that the measured values are acquired in N different energy windows of the detector 2 shown in FIG. 1 relative to a fixedly set spectrum of x-radiation, the detector 2 being able to acquire measured values for at least two different energy ranges of the x-radiation. In addition to the use of such an energy-resolving detector 2, however, it is also possible in a simple way to acquire the measured values relating to different energy ranges of the x-radiation by virtue of the fact that N different spectra of the x-radiation are used. The way in which the spectra are generated is of no consequence at all for the method. For example, it would be conceivable for the computer tomograph to have a plurality of x-ray emitters for this purpose. In this exemplary embodiment, which is not limited, the various spectra are, however, generated by operating the one x-ray tube 1 at differently set tube voltages.

It is assumed below that the object 16, for example a patient, substantially has N=2 components, specifically bone and water. Consequently, two measurements relating to two differently set spectra of the x-radiation are required relative to each projection direction and to each detector element, so that the beam hardening artifacts of the two components can be eliminated.

In the general case, however, it is possible to consider any desired number of different components of the object when correcting the beam hardening artifacts. In principle, the correction of beam hardening artifacts that can be achieved is better the more components of the object that are taken into account.

In order for such a correction of the beam hardening artifacts in a generated image, for example in a tomogram, to be possible, the computer tomograph has a control unit 24 assigned to the gantry and the x-ray emitter 1. The control unit 24 can prescribe various tube voltages such that an object can be trans-irradiated with the aid of differently set spectra of the x-radiation.

The adjustment of the tube voltage is performed as a function of a projection angle position and/or as a function of the rotation of the recording system such that N measured values relating to N different energy ranges of the x-radiation are acquired per projection direction relative to each detector element, it being necessary to select N such that N is greater than equal to two. The measured values acquired by the detector elements 3 are read out in this case by means of an acquisition unit 20 and subsequently transferred to an arithmetic unit 21 for further processing.

In the example set forth here, in which the object 16 essentially includes the two components of bone and water, the measured values are acquired for a first spectrum of the x-radiation and for a second spectrum, differing therefrom, of the x-radiation, the first spectrum being generated being set to a tube voltage of 80 kV, and the second spectrum being generated being set to a tube voltage of 140 kV.

As illustrated in FIG. 2, the arithmetic unit 21 serves the purpose of determining a pseudomonochromatic measured value 8 from two measured values 4, 5 in each case. The pseudomonochromatic measured value 8 is a fictional measured value that would be measured for the object 16 given an imaginary monochromatic x-radiation, and which does not lead to any beam hardening artifacts in a generated image, for example in a tomogram of the computer tomograph.

FIG. 2 show in outline form a determination of the pseudomonochromatic measured value 8 for the purpose of correcting beam hardening artifacts, for example for the two measured values 4, 5 of the detector element 3 acquired relative to different spectra of the x-radiation.

In order to determine the pseudomonochromatic measured value 8, the first step to this end is to determine two transmission thicknesses 6, 7 of the two components of bone and water from the respective two measured values 4, 5 that have been acquired relative to different spectra of the x-radiation. The transmission thicknesses 6, 7 can be determined in a particularly efficient way by use of two lookup tables 9, 10, it being possible to determine a transmission thickness 6, 7 of a component from each of the lookup tables 9 and 10, respectively. The input values of the lookup table 9 or 10 are the two measured values 4, 5, and the output value is the transmission thickness 6, 7 of the respective component.

The pseudomonochromatic value 8 is subsequently synthesized on the basis of the transmission thicknesses 6, 7 thus determined, using the following weighted sum:

$C(m1,m2) = \mu 1 * D1(m1,m2) + \mu 2 * D2(m1,m2)$, wherein $C(m1,m2)$ is the pseudomonochromatic measured value 8, $D1(m1,m2)$ is the first transmission thickness 6 of the first component, specifically water, $D2(m1,m2)$ is the first transmission thickness 7 of the second component, specifically bone, m1 is the first measured value 4 given a first set spectrum of the x-radiation, m2 is the second measured value 5 given a second set spectrum of the x-radiation, $\mu 1$ is the absorption coefficient of the first component, and $\mu 2$ is the absorption coefficient of the second component.

In principle, the pseudomonochromatic measured value 8 can be set freely by selecting the absorption coefficients. The absorption coefficient of the first component expediently corresponds to the absorption coefficient of water, and the absorption coefficient of the second component to the absorption coefficient of bone.

FIG. 2 illustrates in dashed form the general case in which N measured values are acquired relative to N different spectra. From the N measured values, N transmission thicknesses of the N components are read out from corresponding N-dimensional lookup tables such that the pseudomonochromatic value 8 can be synthesized from a weighted sum of the N transmission thicknesses provided by a weighted summer 11. The lookup tables can, however, also be represented for reasons of storage space by appropriate polynomials that describe a mathematical relationship between the input values and the output value of the lookup table.

The N lookup tables 9, 10 are determined by virtue of the fact that firstly the measured values 4, 5 of the x-radiation passing through an object with N components is respectively simulated for each of the N spectra of the x-radiation that can be set, and are stored in the form of an N-dimensional matrix.

By way of example, when simulating measured values for the concrete example of an object with two components, specifically with the components of water and bone, it is necessary that the spectra of the x-radiation can be generated numerically relative to the different tube voltages set during the measurement. To this end, for example, in advance of the simulation the spectra of the x-radiation are measured with the aid of a spectrometer given an appropriately set tube voltage, and stored such that the spectra of the x-radiation can be called up during the simulation.

It would likewise be conceivable to be able to call up a spectrum of an x-radiation in parameterized form during the simulation. The various spectra could, for example, be represented by polynomials of nth order, a variation in the tube voltage prescribed as parameter effecting a displacement of the frequency spectrum of the x-radiation. The stochastic process of the absorption of the x-radiation during passage through the matter or during the passage through the components of the object, the transmission thickness of the respective component being a parameter in the simulation of the measured values, can be carried out with the aid of Monte Carlo simulations, for example. The measured values obtained from the simulation and relating to the various spectra of the x-radiation are acquired in the form of a matrix.

FIG. 3 and FIG. 4 respectively show equipotential lines of simulated measured values of a first and second spectrum of the x-radiation as a function of the transmission thicknesses, present in an object, of two components, the values of the transmission thicknesses of the first component being plotted in the direction of an x-axis shown, and the values of the transmission thicknesses of the second component being plotted in the direction of the y-axis. The measured values exhibit the same value in each case on the equipotential lines illustrated in FIGS. 3 and 4, respectively.

As illustrated in FIG. 3, it is possible for the first measured value 4, which would be generated by the respective detector element 3 in the case of the first set tube voltage or of the first set spectrum of the x-radiation, to be determined from the transmission thickness 6 of the first component in conjunction with the transmission thickness 7 of the second component. As is illustrated in FIG. 4, it is also possible in the same way for the second component of the second measured value 5, which would be generated by the respective detector element 3 given the set second tube voltage or given the second set spectrum of the x-radiation, to be determined from the transmission thickness 6 of the first component in conjunction with the transmission thickness 7 of the second component.

The measured values 4, 5 that can be thus determined are respectively entered as elements into a matrix, the measured values being arranged inside the matrix such that rising values of the transmission thickness 6 of the first component are assigned to the measured values in the illustrated row direction 14, and measured values being assigned rising transmission thicknesses 7 of the second component in the illustrated column direction 15.

The first matrix describes an imaging of the transmission thicknesses 6, 7 of the first and the second components onto the measured value 4 of an x-radiation passing through the object, as a function of the first spectrum of the x-radiation. The second matrix describes correspondingly an imaging of the transmission thicknesses 6, 7 of the first and the second components onto the measured value 5 of an x-radiation passing through the object, as a function of the second spectrum of the x-radiation.

The images defined by the matrices can subsequently be inverted, for example using a numerical method. In a first method step, in this case, there is formed from the image of the first matrix a first auxiliary image in the case of which the transmission thickness 6 of the first component and the measured value 4 dependent on the first spectrum are imaged onto the transmission thickness 7 of the second component. Correspondingly, a second auxiliary image is formed from the image of the second matrix such that the transmission thickness 6 of the first component and the measured value 5 dependent on the second spectrum are likewise imaged onto the transmission thickness 7 of the second component.

Here, it is possible to generate the auxiliary images by reading out a respective value triplet of a) transmission thickness 6 of the first component, b) transmission thickness 7 of the second component and c) measured value 4 or 5 that depends on the first or second spectrum of the x-radiation. It is possible to specify in both auxiliary matrices equipotential lines for which the transmission thickness 7 of the second component has the same values. The auxiliary images can be superposed in pictorial terms such that the equipotential lines of the transmission thicknesses 7 of the second component intersect for specific combinations of the value pair of a) transmission thickness 6 of the first component and b) measured value 4 or 5 of the first or second spectrum of the x-radiation. On the basis of the values of the transmission thicknesses 6, 7 of the first and the second components, and on the basis of the measured values 4, 5 of the first and the second spectra of the x-radiation at the points of intersection of the equipotential lines, it is possible to form the inverted images that specify the relationship between the measured values 4, 5 of an x-radiation passing through the object as a function of the first and the second spectra and the transmission thicknesses 6, 7 of the two components.

Each of these images can be displayed in the form of a modified matrix. The first modified matrix describes an image of the measured values 4, 5 of the x-radiation passing through the object for the first and the second spectra of the x-radiation onto the transmission thickness 6 of the first component. The second modified matrix correspondingly describes an imaging of the measured values 4, 5 of the x-radiation passing through the object for the first and the second spectra of the x-radiation onto the radiation thickness 7 of the second component.

The elements of the modified matrices are finally transferred into lookup tables 9, 10 in each case two measured values 4, 5 relating to the two different spectra of the x-radiation being the input values, and the value read out from the lookup table 9 or 10 respectively corresponding to a transmission thickness 6, 7 of a component.

FIGS. 5 and 6 respectively illustrate the first transmission thickness 6 of the first component and the second transmission thickness 7 of the second component as a function of the first measured value 4 assigned to the first spectrum of the x-radiation and of the second measured value 5 assigned to the second spectrum of the x-radiation, the first measured values being plotted in the direction of the x-axis 12, and the second measured values being plotted in the direction of the y-axis 15. For the sake of clarity, only a first measured value 4 and a second measured value 5 are respectively provided with a reference numeral in FIGS. 5 and 6.

As illustrated in FIG. 5, the first transmission thickness 6 of the first component is determined from the first measured value 4 in conjunction with the second measured value 5. As illustrated in FIG. 6, the second transmission thickness 7 of the second component is determined in the same way from the first measured value 4 in conjunction with the second measured value 5.

In principle, in order to save storage space it is expedient not to calculate all possible quasi-continuous measured values as input values when generating the lookup table. It can happen in this case that a measured value is not present as input value for the lookup table. If a measured value is not covered by the lookup table, the next largest input value and the next smallest input value, which are present in the lookup table, are determined relative to the respective measured value. Subsequently, the associated pseudomonochromatic measured values are read out from the input values thus determined. The pseudomonochromatic measured value corresponding to the measured values being sought is finally determined by an interpolation. The interpolation is preferably implemented by means of a multilinear, for example a bilinear interpolation. However, it is also possible to use other interpolations such as, for example, spline interpolations in the case of which use is made not only respectively of an adjacent entry in the lookup table, but also of a plurality of entries in the lookup table.

As an alternative to the N lookup tables that are used to determine the N transmission thicknesses of the N components of the object in order to determine therefrom the pseudomonochromatic measured value independent of the radiation hardening, it is possible to determine the pseudomonochromatic measured value directly from a single lookup table with in each case N input values and one output value, the single lookup table emerging from N lookup tables by virtue of the fact that the latter are used to synthesize all the pseudomonochromatic measured values for all the possible measured values in the form described above, and are transferred into the single lookup table.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for an x-ray device for suppressing beam hardening artifacts in an image of an object, the method comprising:
   acquiring N measured values relating to N different energy ranges of x-radiation passing through the object, per projection direction relative to each of a number of detector elements of a detector, where N>=2;
   respectively determining one pseudomonochromatic measured value, relative to each of the detector elements, from the acquired N measured values;
   reconstructing an image from the pseudomonochromatic measured values thus determined for the detector elements, in which the beam hardening artifacts are substantially suppressed; and
   displaying the reconstructed image,
   wherein the determination of the pseudomonochromatic measured value from the N measured values includes a determination of N transmission thicknesses of N different components of the object, the N different components of the object having differing energy dependencies of the absorption coefficients.

2. The method as claimed in claim 1, wherein the N measured values relating to the N different energy ranges are issued from N differently set spectra of the x-radiation.

3. The method as claimed in claim 1, wherein the N measured values relating to the N different energy ranges are acquired by an energy-resolving detector in N different energy windows.

4. The method as claimed in claim 1, wherein the pseudomonochromatic measured value is calculated from a sum of the N transmission thicknesses, weighted in each case with a weighting coefficient, of the N different components.

5. The method as claimed in claim 4, wherein the weighting coefficient of the transmission thickness is an absorption coefficient of the respective component.

6. The method as claimed in claim 1, wherein the N transmission thicknesses are determined from N lookup tables with in each case N input values and one output value, the N input values being the N measured values, and the output value being the transmission thickness of the respective component.

7. The method as claimed in claim 6, wherein the N lookup tables are determined by virtue of the fact that the N measured values relating to the N different energy ranges are simulated and stored in the form of an N-dimensional matrix, the transmission thicknesses of the N different components being varied during the simulation, and the N-dimensional matrices thus determined subsequently being transformed into modified matrices that belong to inverted imagings of the image, defined by the N-dimensional matrices, of N measured values onto N transmission thicknesses, one of the N lookup tables being formed from each of the N modified matrices.

8. The method as claimed in claim 6, wherein the pseudomonochromatic measured value is interpolated from entries of the respective lookup table.

9. The method as claimed in claim 8, wherein the interpolation of the pseudomonochromatic measured value is a multilinear interpolation.

10. The method as claimed in claim 6, wherein the respective lookup table is represented by a polynomial that describes a mathematical relationship between the input values and the output value of the lookup table.

11. The method as claimed in claim 1, wherein the pseudomonochromatic measured value is determined directly from a single lookup table with in each case N input values and one output value, the N input values being the N measured values, and the output value being the pseudomonochromatic measured value.

12. The method as claimed in claim 1, wherein the x-radiation is generated by an x-ray emitter in the form of an x-ray tube.

13. The method as claimed in claim 12, wherein the N measured values relating to the N different energy ranges of the x-radiation are generated by differently set tube voltages.

14. The method as claimed in claim 13, wherein N=2, and wherein a first spectrum of the x-radiation is generated for the purpose of acquiring in each case a first measured value with the tube voltage set to 80 kV, and a second spectrum of the x-radiation is generated for the purpose of acquiring a second measured value with the tube voltage set to 140 kV.

15. A computer tomograph comprising at least one device for carrying out the method of suppressing beam hardening artifacts from images of an object, as claimed in claim 1.

16. A computer-readable medium including a computer program, which when executed on a computer, causes the computer to carry out the method as claimed in claim 1.

17. The method as claimed in claim 1, wherein the N different components have different absorption properties based on different mean atomic numbers for thicknesses.

18. The method as claimed in claim 1, wherein the N different components include at least one of biological tissues and fluids.

19. The method as claimed in claim 1, wherein the N different components include biological tissues and fluids, the biological tissues including bone and the fluids including water.

20. A computer tomograph, suppressing beam hardening artifacts in an image of an object, comprising:

means for acquiring N measured values relating to N different energy ranges of x-radiation passing through the object, per projection direction relative to each of a number of detector elements of a detector, where N>=2;

means for respectively determining one pseudomonochromatic measured value, relative to each of the detector elements, from the acquired N measured values;

means for reconstructing an image from the pseudomonochromatic measured values thus determined for the detector elements, in which the beam hardening artifacts are substantially suppressed; and means for displaying the reconstructed image, wherein the determination of the pseudomonochromatic measured value from the N measured values includes a determination of N transmission thicknesses of N different components of the object, the N different components of the object having differing energy dependencies of the absorption coefficients.

* * * * *